United States Patent
Fearnot et al.

(10) Patent No.: US 9,393,378 B2
(45) Date of Patent: Jul. 19, 2016

(54) APPARATUSES AND METHODS FOR COOLING SPECIFIC TISSUE

(75) Inventors: Neal E. Fearnot, West Lafayette, IN (US); Jesper Thyregod Nielsen, Roskilde (DE)

(73) Assignee: Muffin Incorporated, West Lafayette, IN (US)

( * ) Notice: Subject to any disclaimer, the term of this patent is extended or adjusted under 35 U.S.C. 154(b) by 677 days.

(21) Appl. No.: 13/610,930

(22) Filed: Sep. 12, 2012

(65) Prior Publication Data
US 2013/0000642 A1    Jan. 3, 2013

Related U.S. Application Data

(63) Continuation of application No. PCT/US2011/028475, filed on Mar. 15, 2011.

(60) Provisional application No. 61/313,865, filed on Mar. 15, 2010.

(51) Int. Cl.
*A61M 16/10* (2006.01)
*A61M 16/06* (2006.01)
*A61M 19/00* (2006.01)
(Continued)

(52) U.S. Cl.
CPC ........... *A61M 16/1075* (2013.01); *A61M 16/06* (2013.01); *A61M 19/00* (2013.01); *A61F 7/12* (2013.01); *A61F 2007/0002* (2013.01); *A61F 2007/0063* (2013.01); *A61F 2007/0064* (2013.01); *A61F 2007/0096* (2013.01); *A61F 2007/0228* (2013.01); *A61M 16/0461* (2013.01); *A61M 16/0683* (2013.01); *A61M 2016/0039* (2013.01); *A61M 2202/0208* (2013.01); *A61M 2205/3368* (2013.01); *A61M 2205/362* (2013.01); *A61M 2205/3606* (2013.01); *A61M 2210/0693* (2013.01)

(58) Field of Classification Search
CPC ............ A62B 7/02; A62B 7/04; A62B 18/02; A62B 18/08; A62B 9/003; A61M 16/1075; A61M 16/1095; A61M 2205/3606; A61M 16/06; A61M 16/0461; A61M 16/0666; A61M 19/00; A61M 2202/0208; A61M 2205/362; A61M 2210/0693; A61F 7/12; A61F 2007/0002
USPC ........................................ 128/205.22, 204.15
See application file for complete search history.

(56) References Cited

U.S. PATENT DOCUMENTS 5,023,023 A * 6/1991 Elenewski ..................... 264/1.7
5,542,413 A * 8/1996 Horn ......................... 128/204.15
(Continued)

FOREIGN PATENT DOCUMENTS

FR          2923722 A1    5/2009
WO   WO 2008/094505 A1    8/2008

*Primary Examiner* — Valerie L Woodward
(74) *Attorney, Agent, or Firm* — Woodard, Emhardt, Moriarty, McNett & Henry LLP

(57) ABSTRACT

Among other things, there is provided a system for providing therapeutic cooling or hypothermia to localized areas of the body such as the brain. A source of compressed gas such as a medical-use oxygen canister is connected via a delivery tube to a mask fitted to a patient. The gas undergoes adiabatic cooling as it enters the delivery tube, and is provide to the patient in such cooled state. The system may be provided as a portable or ambulatory device or kit, with the delivery tube or other part easily disconnected from one compressed gas source and connected to another, for continued therapy even during transportation.

23 Claims, 6 Drawing Sheets

(51) Int. Cl.
*A61F 7/12* (2006.01)
*A61F 7/00* (2006.01)
*A61F 7/02* (2006.01)
*A61M 16/04* (2006.01)
*A61M 16/00* (2006.01)

(56) References Cited

U.S. PATENT DOCUMENTS

| | | | |
|---|---|---|---|
| 5,584,289 A * | 12/1996 | Wise | 128/205.24 |
| 5,676,135 A * | 10/1997 | McClean | 128/205.22 |
| 6,983,749 B2 * | 1/2006 | Kumar et al. | 128/204.15 |
| 7,255,107 B1 * | 8/2007 | Gomez | 128/207.13 |
| 8,721,699 B2 * | 5/2014 | Barbut et al. | 607/105 |
| 2005/0016540 A1 * | 1/2005 | Jumpertz | 128/205.22 |
| 2006/0201512 A1 * | 9/2006 | Garrett et al. | 128/206.11 |
| 2007/0123813 A1 | 5/2007 | Barbut | |
| 2008/0015543 A1 | 1/2008 | Wang | |
| 2008/0023002 A1 * | 1/2008 | Guelzow et al. | 128/201.24 |
| 2008/0035145 A1 * | 2/2008 | Adams | A62B 18/08 128/204.18 |
| 2011/0253136 A1 * | 10/2011 | Sweeney et al. | 128/203.12 |

\* cited by examiner

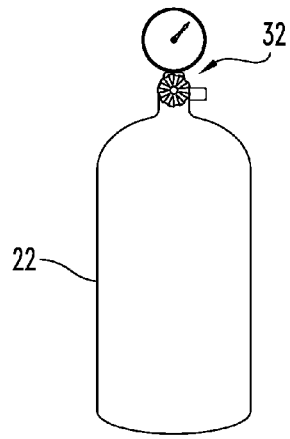
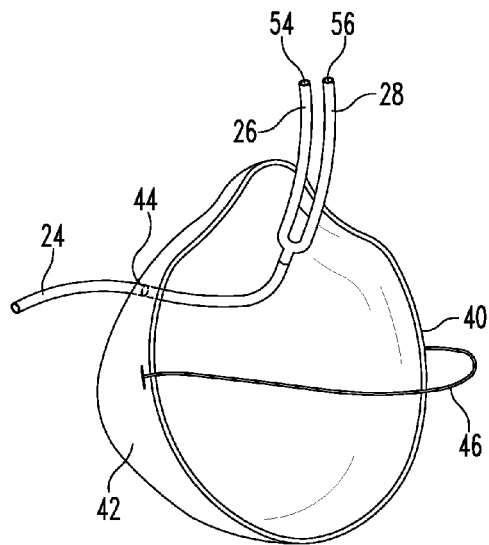
Fig. 2  Fig. 3A
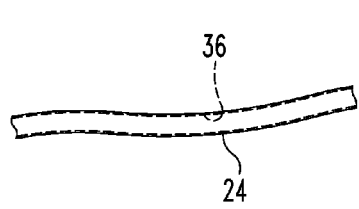
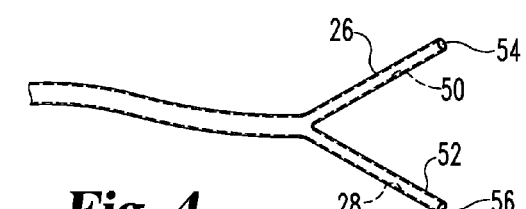
Fig. 4
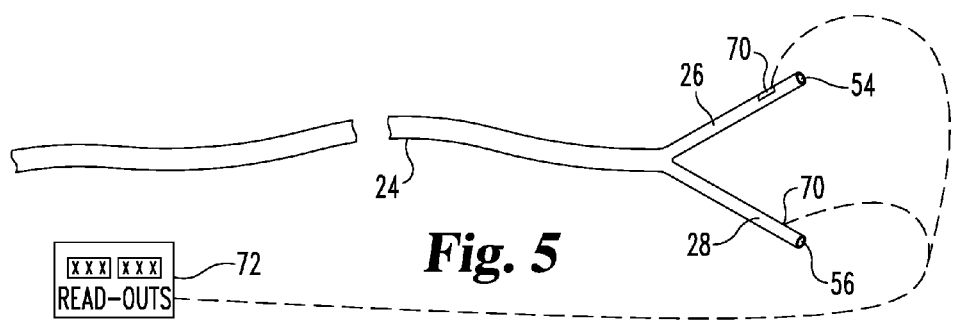
Fig. 5

APPARATUSES AND METHODS FOR COOLING SPECIFIC TISSUE

REFERENCE TO RELATED APPLICATIONS

This application is a continuation of International Application No. PCT/US2011/028475, filed Mar. 15, 2011, pending, which claimed the benefit of U.S. Provisional Patent Application No. 61/313,865, filed Mar. 15, 2010, abandoned, each of which is herby incorporated by reference.

The present disclosure concerns apparatuses and methods useful for providing cooling to particular tissues or body parts. In particular, it concerns a faster, less complicated system and techniques for cooling internal tissues or organs, such as the brain, so as to reduce or limit damage.

BACKGROUND

Therapeutic hypothermia, i.e. lowering a patient's body temperature, has been used as a treatment to help reduce the risk of the ischemic injury to tissue following a period of insufficient blood flow, e.g. following a cardiac arrest or stroke. Different systems and methods for inducing such hypothermia have been proposed, such as submersion or enclosure of the body in a cooling bath or wrap, or by routing blood flow out of the body and through a cooling device. In other systems, external cooling of the head through placement of a cap, helmet or collar with cooling mechanisms or flow is proposed. Other approaches have included spraying a volatile liquid perfluorocarbon coolant into the nasal cavity, with evaporation of the coolant decreasing the temperature in the head, or expanding a balloon against internal airway tissues, e.g. with cold liquid.

However, such systems for cooling are not optimal for the purpose of cooling the brain or other specific tissues. Whole-body cooling by way of a bath or wrap risks damage to skin, muscle or other tissues if not carefully administered. It also requires bulky or relatively large devices to cover the body, and overuses cooling insofar as generally the entire body need not be subjected to hypothermia in order to treat the brain or other localized tissues. Routing blood through an external cooling device requires not only sophisticated equipment but also can only be done for a limited time, e.g. the amount of time a patient can sustain a cardiopulmonary bypass. External cooling of the head requires an external fitting that generally must fit closely with the patient's head and/or neck, requiring a number of sizes or adjustability for different patients. It can have also substantial inefficiencies in cooling because of its exposure to the ambient environment. Use of a volatile coolant within the body can present difficulties in terms of monitoring potential toxicity levels of the coolant and ensuring that the coolant remains in parts of the body that will tolerate it. A balloon that seals the airway may not be usable over significant time periods due to its interference with the patient's breathing.

Accordingly, new devices and methods for applying cooling to specific tissues, for example to treat the brain and protect it from adverse effects arising from lack of blood flow (e.g. stroke or cardiac arrest) or from traumatic injury, are needed.

SUMMARY

The present disclosure includes, among other things, an apparatus that includes a source of coolant consisting essentially of compressed breathable gas and a delivery tube having a proximal end connected to the source of coolant. When gas is released from the source into the proximal end of the delivery tube, the gas cools adiabatically, and the delivery tube is configured such that the gas passes through the delivery tube without substantial gain of thermal energy, e.g. without gaining more than 20 Celsius degrees, or more than about 1 to 5 Celsius degrees, in temperature. At least one insertion tube is connected to the delivery tube and extends to a free end having an opening. The insertion tube(s) are sized and configured to be inserted into a patient's nose so that the free end is positioned in the patient's airway beyond the anterior turbinate area of the patient's nose, and so the gas passes the mucosa and conchae of the nose before exiting the insertion tube(s). The gas experiences no further cooling between the proximal end of the delivery tube and the at least one insertion tube.

In some embodiments, the source of gas is a canister of compressed breathable gas, which may be portable by hand (e.g. small medical-use canister), or a non-portable stand-alone tank. A mask may be provided to cover at least the patient's nose and to be held to the patient's head, so that at least one of the delivery tube and insertion tube(s) extend through the mask with the mask resting against the patient's face when the at least one insertion tube is inserted into the patient's nose. The noted configured condition of the delivery tube may include the length of the delivery tube being about one foot or less, the material of the delivery tube being of insulation (e.g. foam insulation), and/or the delivery tube having an outer layer of insulation. The source of gas may be more than one compressed gas canister, e.g. two compressed gas canisters with a Y-shaped connector connected to the delivery tube and to each of the canisters. A two-way stopcock may be connected to each of the canisters and to the delivery tube.

In other embodiments, a system for cooling the brain with compressed gas disclosed, which can include a supply of a compressed breathable gas for thermal transfer with tissues in a patient's head, with the gas provided in at least one canister initially at a first pressure greater than atmospheric pressure. A set of first and second nasal tubes each for insertion into a respective nostril of a patient may each have a respective distal end with a respective hole, and be sized and configured so that when they are fully inserted into the patient, their respective distal ends are positioned in one or more of the choanae of the patient. A delivery tube connects the canister(s) with the nasal tubes and may be configured such that gas traveling along the delivery tube remains at approximately the same temperature along the tube. As the gas enters the delivery tube, the gas is cooled adiabatically to a first temperature below room temperature. The gas flows through the delivery tube and nasal tubes without any added liquid to exit the respective holes of the nasal tubes at approximately the first temperature, to cool tissues adjacent the brain cavity.

In certain embodiments the system can include at least one regulator connected to the at least one canister and to the delivery tube. Adiabatic cooling of the gas as it enters the delivery tube from the regulator(s) cools the gas to a first temperature of between about 0° and 20° Celsius, and the gas exits the nasal tubes at a second temperature not less than the first temperature and between about 0° and 20° Celsius. The supply of breathable gas is sufficient in flow, temperature and duration to cool at least a portion of the brain by about 1 to 5 Celsius degrees. The supply can be provided by multiple canisters of compressed gas, with the delivery tube is adapted to easily accept flow from multiple canisters. The delivery tube may be connected to a stopcock, with the stopcock connected to the multiple canisters of compressed gas and operable to switch flow into the delivery tube between or among the multiple canisters. The configured condition of the delivery tube may include a layer of insulation incorporated in or on the delivery tube.

Also disclosed is a cooling system for applying localized hypothermic treatment, including a heat-transfer medium consisting essentially of a breathable gas supplied in a canister at a pressure greater than atmospheric pressure. The gas does not have in it or propel any liquids. A delivery tube is connected to the canister, and is configured so that the gas can travel along it without a significant change in temperature of the gas along the delivery tube's length. A pair of insertion tubes is connected to the delivery tube and are sized and configured so that respective distal ends of each insertion tube are in the choanae of the patient when the insertion tubes are fully inserted into the patient. The canister may be of a hand-portable size and weight, so that the system is carryable to a patient by an emergency responder. The configured condition of the delivery tube can include forming the delivery tube entirely of an insulation, such as foam insulation. The insertion tubes may each have a single outlet at their respective distal ends so that the gas exits the tubes in one direction.

The disclosure includes a compressed gas source (e.g. $O_2$, $N_2$) that may be attached to a regulator (either integrally or via high pressure tubing), with the output tubing from the regulator extending to a mask that is placed over the patient's mouth and nose. The delivery tube extends into the mask and diverges as a pair of smaller tubes that are inserted into the nasal cavity to deliver cold gas directly to the front of the sinus region. The nasal cavity tubes are of a longer length than standard nasal tubes for oxygen delivery so that they bypass or open beyond the anterior turbinate area of the nose, in which the greatest transfer of heat from the nasal mucosa to the incoming airflow has been shown to occur, thereby helping to better preserve the temperature of the cold gas being introduced. The nasal tubes are shorter than spray tubes in systems used to deliver volatile chemicals into the nose as spray via side ports, which spray tubes extend all the way to the back of the sinus region, so that contact with the sinus is maximized.

Systems for therapeutic cooling as disclosed herein and indicated above can thus include a mask having a strap and a hole, with the mask adapted to cover at least the patient's nose (and perhaps eyes, mouth and/or other parts of the face or head) and to be held to the patient's head by the strap. When the mask rests against the patient's face a space between at least a portion of the patient's face and the mask exists. A source of coolant, e.g. solely or essentially compressed breathable gas, and a flow path from that source through the mask's hole of said mask, can be provided. A regulator may be in the flow path between the coolant source and the hole, and a delivery tube having a lumen defines at least part of the flow path for conducting the coolant toward the mask. At least one sensor may be connected to one or more of the delivery tube, regulator and mask, and a readout is communicatively connected to the sensor(s) to provide information concerning the coolant. The coolant is cooled adiabatically after release from the source.

The source is a canister of compressed breathable gas in particular embodiments, with the canister being portable by hand or a stand-alone tank as examples. Insertion tubes may be connected to the delivery tube, for example with each extending to a respective free end having an opening and/or with each sized and configured to be inserted into respective nares of a patient's nose so that said free ends are positioned in the airway beyond the anterior turbinate area of the patient's nose. In such cases, the gas passes the mucosa and conchae of the nose before exiting the insertion tubes. At least one of the delivery tube or insertion tubes extend through the mask's hole so that the mask rests against the patient's face when at least one insertion tube is inserted into the patient's nose. Some embodiments include a configured condition of the delivery tube in which a length of the delivery tube is about one foot or less. Other exemplary configured conditions of the delivery tube include forming it of foam insulation, and/or of forming it of an internal plastic lumen with an outer layer of foam insulation. The source can include two compressed gas canisters. In such cases, the system may also include one or both of a Y-shaped connector connected to the delivery tube and to each of the canisters, and a two-way stopcock connected to each of the canisters and to the delivery tube.

The regulator is fixed in particular embodiments to the mask so that an output of the regulator communicates with the mask's hole, with adiabatically-cooled gas from the regulator entering the mask. A high-pressure tube from said source to said regulator may be used. In various mask embodiments, the mask can cover the eyes and/or mouth of a patient as well as the nose, and may be a full-face mask. The readout can be fixed to the mask while the mask permits observation of the patient's eyes when fitted to the patient, so that the patient's eyes and the readout are both within an observer's field of vision when the mask is fitted to the patient.

A system for cooling the brain with compressed gas can also be characterized as having a supply of a compressed breathable gas for thermal transfer with tissues in a patient's head, provided in at least one canister initially at a first pressure greater than atmospheric pressure, and a mask for fitting over a patient's face to cover at least the patient's nose and eyes, the mask having a regulator fitted to it. A high-pressure delivery tube connects the canister(s) with the regulator, and the delivery tube is configured such that gas traveling along it remains at approximately the same temperature. The gas is cooled adiabatically by passage through the regulator to a first temperature below room temperature, and it flows into the mask at approximately the first temperature to cool tissues adjacent the brain cavity. In some embodiments, a set of first and second nasal tubes each for insertion into a respective nostril of a patient are provided, such tubes each having a respective distal end with a respective hole, and each being sized and configured so that when they are fully inserted into the patient, the respective distal ends are positioned in one or more of the patient's choanae. The first temperature, for example, is between 0 and 20 degrees Celsius. The supply of breathable gas may be sufficient in flow, temperature and duration to cool at least a portion of the brain by about 1 to 5 Celsius degrees. In particular embodiments, the supply is provided by multiple canisters of compressed gas, with the delivery tube adapted to easily accept flow from multiple canisters. For example, the delivery tube may be connected to a stopcock, which is connected to multiple canisters of compressed gas, with the stopcock operable to switch flow into the delivery tube between or among the canisters. As above, a configured condition of the delivery tube can include a layer of insulation incorporated in or on the delivery tube.

A cooling system for applying localized hypothermic treatment may include a heat-transfer medium consisting essentially of a breathable gas, with the gas supplied in at least one canister at a pressure greater than atmospheric pressure. A delivery tube is connected to the canister(s) and is configured so that the gas can travel along the delivery tube without significant change in temperature of the gas along the length of the delivery tube. A mask has a regulator that is connected to the delivery tube so that the regulator's output flows into the mask, and a readout display that shows information related to the operation of the system, which information may come from one or more sensors (e.g. flow-rate or temperature sensors) in the mask, delivery tube, or other parts of the system. A stopcock is connected to the delivery tube and is operable to change flow into the delivery tube from a first canister to a second canister. As noted above, embodiments can include a pair of insertion tubes connected to the delivery tube and sized and configured so that respective distal ends of each of them are in the patient's choanae when the insertion tubes are fully inserted into the patient. The canister(s) may be of a hand-portable size and weight, so that the system is carryable to a patient by an emergency responder. The configured condition of the delivery tube may include forming it entirely of a foam insulation, and if used, insertion tubes may each have a single outlet at their respective distal ends so that gas exits the tubes in one direction.

Tubing length for current respiratory oxygen delivery systems is selected to maximize warming of the oxygen as it is released from the source tank and flows to the nasal tubing. In the present system, the length of that tubing is shortened as much as possible, in one embodiment about a foot in length, to maintain the low temperature or negative thermal energy of the gas. To further limit the effect of ambient warming of the gas flow or warming from direct contact with the patient, the delivery tubing and/or nasal tubing may be clad with insulation such as foam or another suitable material that limits heat transfer. With the delivery tubing shortened to limit heat transfer and the nasal tubing lengthened to limit warming of the gas by the nasal cavity, the lowest available temperature of gas is delivered to the sinus for maximum therapeutic benefit. The present system may be configured in a unit as an emergency kit that can be used by an EMT or kept at a business or other site, such as mounted to a wall alongside an AED (automated external defibrillator). The size of the medical gas canister or cylinder varies according to the intended use of the device, e.g. whether it is to treat a stroke victim prior to arrival of emergency help (e.g. about a ten or fifteen minute supply), or for during transport to a hospital until other measures can be taken. Of course, gas canisters or bottles can be exchanged as they are depleted.

These and other features are described in detail below, disclosing a less complicated, more elegant and more portable or ambulatory solution for providing more direct therapeutic cooling to particular tissues, e.g. the brain to combat ischemia due to stroke, cardiac arrest or other causes, swelling due to trauma, or other damage. Handling of volatile chemicals, provision of sophisticated mixing or monitoring apparatus, incorporation of electrical or other external cooling or refrigeration items, insertion of balloons or other airway-blocking structure, and other complications are unnecessary, and embodiments of the present disclosure are easily portable and accessible when and where needed.

BRIEF DESCRIPTION OF THE DRAWINGS

FIG. 2 is an embodiment of a gas canister of the embodiment of FIG. 1.

FIG. 3A is a perspective view of an embodiment of mask structure in the embodiment of FIG. 1.

FIG. 4 is an embodiment of a delivery tube in the embodiment of FIG. 1.

FIG. 5 is an embodiment of a delivery tube as in FIGS. 1 and 4, with additional structure.

DESCRIPTION OF THE ILLUSTRATED EMBODIMENTS

Figure 1:
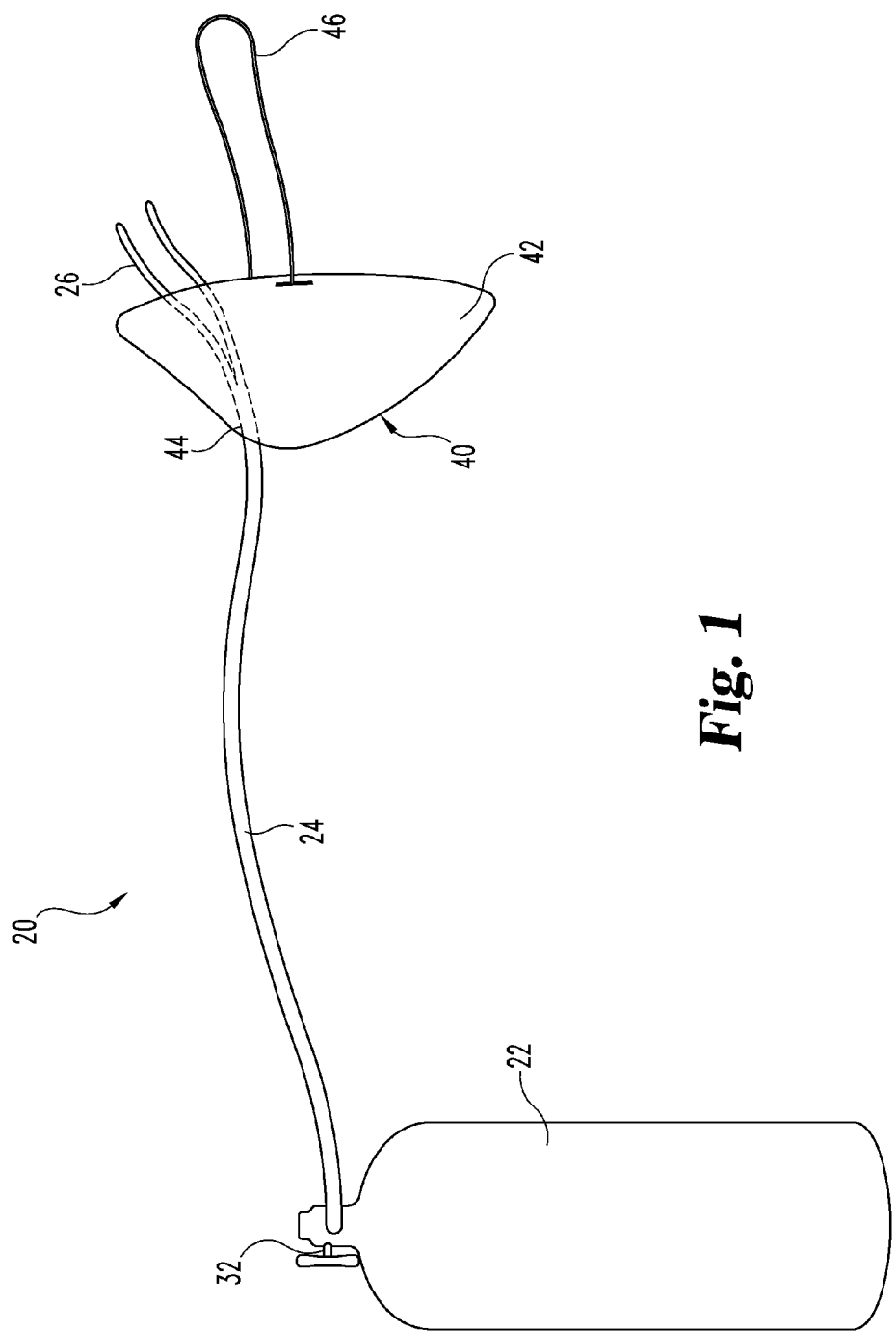
FIG. 1 is a representation of an embodiment of a system according to the present disclosure.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, and alterations and modifications in the illustrated device, and further applications of the principles of the disclosure as illustrated therein are herein contemplated as would normally occur to one skilled in the art to which the disclosure relates.

Referring generally to the drawings, there is shown an embodiment of a system 20 for cooling particular tissues in the human or animal body. Throughout the following discussion, the cooling of the brain as part of a therapy for treating brain ischemia is noted as an example of a treatment method and of the use of system 20. It will be understood that cooling of other particular parts of the body can also be performed using system 20.

In the illustrated embodiment, system 20 includes a source of compressed gas, such as a canister 22, a delivery tube 24 connected to canister 22, and a pair of insertion tubes 26, 28 connected to delivery tube 24. In general, as discussed further below, gas flows in a flow path from canister 22 or other source through delivery tube 24 (and insertion tubes 26, 28, if provided) and to the patient.

Canister 22 in the illustrated embodiment is a standard container for holding a gas in a pressurized state. Accordingly, canister 22 has a valve or regulator 32 and an opening 34 for allowing gas to be released from canister 22 at one or more flow rates or pressure levels. For example, item 32 may be a regulator designed to step the pressure in canister 22 down to a lower pressure that is above atmospheric pressure. Standard tanks, cylinders or other canisters commonly contain gases pressurized to about 2000-6000 psi, and regulator 32 may step that pressure down to a level above atmospheric pressure (14.7 psi or 760 mmHg) that will allow steady, non-injurious flow of gas into and through delivery tube 24. In some embodiments, valve or regulator 32 may be connected to canister 22 or other gas source via high-pressure tubing or conduit, rather than being fixed to or integrally with canister 22, e.g. to a mask as noted further below.

Canister 22 may be of any size appropriate to delivering gas in a therapeutic setting. In particular embodiments, canister 22 is a portable cylinder or bottle containing an amount of gas sufficient for a short term (about ten to fifteen minutes) supply at the flow rate(s) or pressure level(s) permitted by valve or regulator 32. As one example, canister 22 may be a standard C, D, or E cylinder having an appropriate CGA (Compressed Gas Association)-standard connection. In other embodiments, canister 22 may be a tank of approximately the size of a portable breathing tank for firefighters or scuba-divers, or of approximately the size of stand-alone tanks found in laboratories. In the latter case, it will be understood that such tanks are not portable by hand, but may be stationed at an appropriate location in a building (e.g. a hospital) or a vehicle (e.g. an ambulance).

The gas within canister 22 is a breathable gas, i.e. one compatible with administration into a patient's airway and sinus passages, so that as administered it is non-toxic and provides little or no chemical or biological damage to tissues along the respiratory system or other parts of the body. In particular embodiments, the gas is air, a molecular gas such as oxygen ($O_2$) or nitrogen ($N_2$), an enriched air nitrox, heliox, or combinations of one or more of those gases with each other or with other gases. In certain embodiments, the gas within canister 22 is substantially pure, having no significant percentages of other undesired gases, and no biologically active ingredients. The gas within canister 22 is at a pressure that depends on the fullness of canister 22 but is significantly greater than atmospheric pressure, and as already noted, in some embodiments gas within a substantially full canister 22 is at a pressure of about 2000-6000 psi, or at pressures common to medical-use gas canisters. Accordingly, in one embodiment canister 22 is a medical-grade or medical-use canister or tank filled with oxygen and which has a valve or regulator 32 fixed or otherwise connected to it for stepping the pressure of the oxygen down to a pressure greater than atmospheric pressure.

Delivery tube 24 is connected to canister 22 (e.g. at a valve or at regulator 32, if provided) and includes a central lumen 36 in this embodiment for transfer of gas from canister 22. Delivery tube 24 is flexible and relatively lightweight in the illustrated embodiment, so as to permit easy movement and arrangement of tube 24 according to the needs of the patient and user of system 20. In particular embodiments, delivery tube 24 is or includes a tube of polyvinyl chloride (PVC) or similar material capable of handling continuous gas flow without rupture or significant leakage. Delivery tube 24 also has good insulating properties in certain embodiments, limiting heat transfer from the environment to gas within lumen 36. Accordingly, if tube 24 is of only one layer forming lumen 36, then the material should have good resistance to heat conductance and/or the thickness of the layer should minimize heat transfer between lumen 36 and the environment outside of tube 24. In particular, the tube material should prevent heat from being transferred from outside tube 24 into lumen 36. For example, tube 24 may be of a material such that the thickness of the material necessary to keep heat transfer at a minimum will not form a tube too large to be inserted into a patient's nose.

In specific embodiments, insulation may be a part of or incorporated into tube 24 (and/or tubes 26, 28, discussed further below). For example, tube 24 may be formed entirely of a foam insulation, as by extrusion. Further, more than one layer may be included in tube 24 to increase its insulating properties, or one or more layers of foam or other insulation 38 may be provided around or at least partially mixed with tube 24 along some or all of its length. For example, tube 24 can be made through a coextrusion of a thin layer 39 of PVC or similar material (forming an internal lumen L) with an external layer of foam insulation 38. Such a tube has gas-nonpermeability qualities of PVC internally while being softer and more comfortable or less-potentially injurious to the patient and insulated externally. Such embodiments of tube 24 prevent significant warming of gas from canister 22 as it travels through lumen 36 in delivery tube 24.

Delivery tube 24 extends to or through a mask 40, in particular embodiments, that is adapted for placement over at least the nose and perhaps other parts of the face of a patient (e.g. eyes and/or mouth) for convenience and security in holding tube 24 and administering cooling to the patient. In the illustrated embodiments, mask 40 has a body 42 with a hole 44 in the front through which a portion of delivery tube 24 extends, and a strap 46 attached to opposing sides of body 42 for holding mask 40 to the face of the patient. Hole 44 is of approximately the same size as the outer diameter of delivery tube 24. A washer, valve, O-ring or other sealing or holding member (not shown) may be provided in or adjacent to hole 44 so as to form at least a minimal seal between mask 40 and delivery tube 24, and/or to keep tube 24 from moving or moving significantly with respect to mask 40. Mask 40, 40' may be of a plastic, substantially gas-impermeable material, and may be such as is used over a patient's nose and mouth to provide oxygen to comatose or less-responsive patients (e.g. FIG. 3A), or other types of masks such as those covering the eyes and nose (e.g. FIG. 3B). Each provides a space between the mask and the face of the patient when the mask is fitted to the patient. As previously indicated, mask 40 is intended to cover at least a portion of the face to enable cooling gas to be administered to the patient.

In the former case (FIG. 3A), body 42 is generally circular or oval in shape to cover at least the nose and mouth of the patient. Hole 44 is in the middle or upper area of mask 40 to be generally adjacent the patient's nose when mask 40 is fitted. Delivery tube 24 diverges inside mask 40 into insertion tubes 26, 28. Insertion tubes 26, 28 are parts of delivery tube 24 that branch off for insertion into the body, and each tube 26, 28 has its own lumen 50, 52. Lumens 50, 52 are centrally located within respective tubes 26, 28 and communicate with or continue on from lumen 36 of tube 24 in this embodiment. In other embodiments, insertion tubes 26, 28 may be made separately from delivery tube 24, as by joining tubes 26, 28 in a base or stem to form a generally Y-shaped structure, which is attached (e.g. welded or otherwise sealed) to the end of delivery tube 24 within mask 40.

Figure 3B:
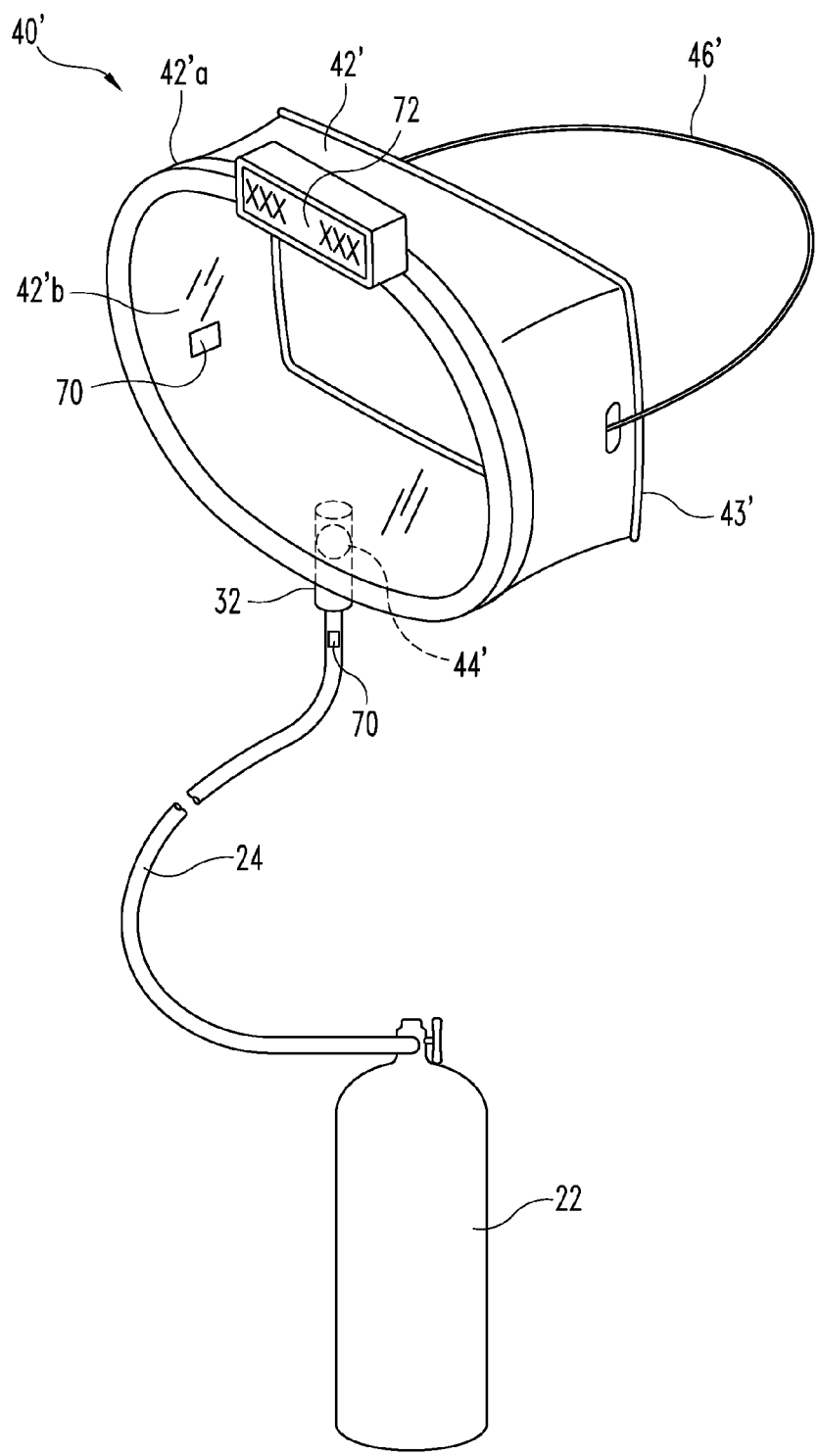
FIG. 3B is a perspective view of an embodiment of another type of mask structure useful in the embodiment of FIG. 1.
Figure 6:
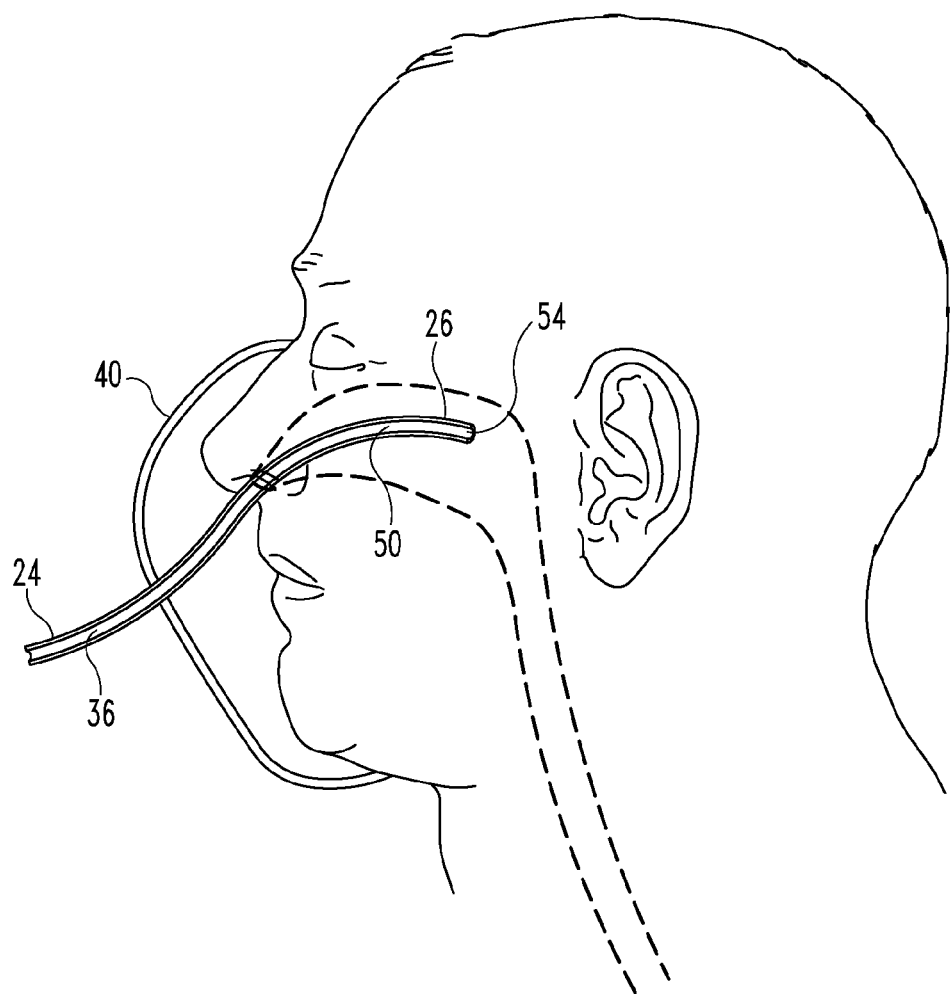
FIG. 6 is a schematic representation of a portion of the embodiment shown in FIG. 1 in cross section and applied to a patient.
Figure 7A:
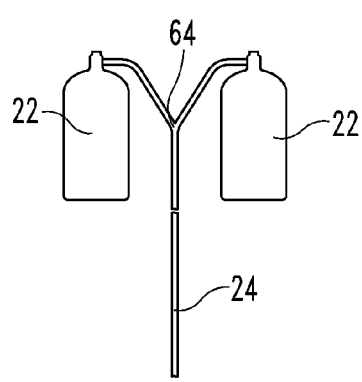
FIG. 7A is a representation of a portion of a system as in FIG. 1 with an embodiment of a connection between gas canisters and a delivery tube.
Figure 7B:
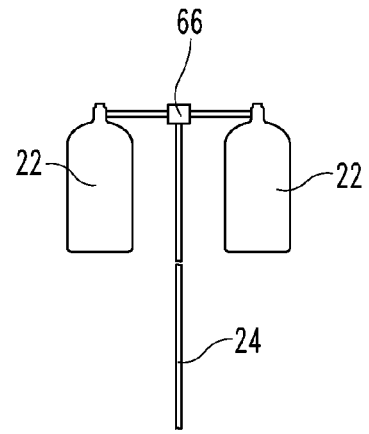
FIG. 7B is a representation of a portion of a system as in FIG. 1 with another embodiment of a connection between gas canisters and a delivery tube.
Figure 8:
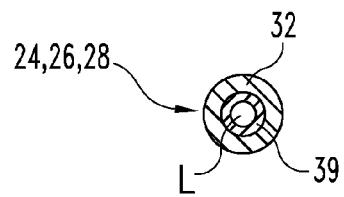
FIG. 8 is a cross-sectional representation of a tube or portion thereof indicated in FIG. 1 in a particular embodiment.

In the latter case, mask 40' may be generally in the form of a scuba-type mask (FIG. 3B). Mask 40' includes a body 42' with a hole 44', and a strap 46' for passing around or over the patient's head to maintain mask 40' against the patient's face. Body 42' is sized and configured to cover at least the patient's nose and eyes. The illustrated embodiment of mask 40' includes a sealing member 43' around the portion of mask 40' that contacts the face, and sealing member 43' may be in the form of a skirt or compressible rubber, latex or plastic edge. Sealing member 43', under the force provided by strap 46' in holding mask 40' to the face, provides an fluid-tight (e.g. airtight) seal between body 42' and the patient's face. Body 42' may be closed or unitary, i.e. one-piece, or it can have an outer frame 42'*a* and an inner portion or insert 42'*b*. In a particular embodiment of the latter case, inner portion 42'*b* is generally in front of the patient's eyes when mask 40' is fitted to the patient. One or more vents (not shown) may be included in body 42' (including either or both of frame 42'*a* and inner member 42'*b*, if present) to permit venting of the space inside mask 40', should it be necessary for any reason to remove the cooled gas from inside mask 40' or to otherwise affect or alter the environment within mask 40'. Inner portion 42'*b* has a fluid-tight or airtight seal with frame 42'*a* and may be transparent to permit a physician, medical technician or other professional to observe the patient's eyes and facial tissue during treatment. While mask 40' is illustrated in an embodiment that covers the eyes and nose of a patient, it will be understood that other embodiments may cover eyes, nose and mouth, or be a full-face mask.

Hole 44' is in a relatively central location in mask 40', and may act as or include an inlet or port for gas from canister 22 or other gas source. As indicated above, a regulator 32 may be located away from a canister 22 but connected to it via high-pressure tubing or conduit, and as shown in FIG. 3B regulator 32 is connected or fixed to mask 40' so that the outlet or output of regulator 32 communicates with hole 44'. In other embodiments, a short tube (not shown) may connect the outlet of regulator 32 with hole 44'. The flow path for gas extends from the source (e.g. canister 22) through tube 24 and regulator 32 to mask 40'. High-pressure gas flows to and through regulator 32, being stepped down in pressure (and reduced in temperature) and directly flowing into the interior of mask 40'. In such an embodiment, in which mask 40' is provided with an attached regulator 32 and tube 24 is formed of high-pressure tubing, mask 40' is easily disconnected from an empty gas source (e.g. a canister) and reconnected to a full canister or other source.

Mask 40' in the illustrated embodiment does not include insertion tubes 26, 28, although it will be understood that other embodiments could include such tubes arranged and utilized as described herein. Without insertion tubes 26, 28 to carry gas into the nose, the internal space of mask 40' (inside of mask 40', between itself and the patient's face) contains cooling gas. Some of the gas is inhaled through the nose, while some remains in the space over the patient's eyes, cheeks, nose and perhaps other facial parts enclosed by mask 40'. Inhaled gas passes through the nose to the choanae to provide cooling. In this embodiment, the temperature of the gas flowing into mask 40' can be somewhat cooler than may be provided for mask 40, because there will be some warming of the gas as it passes through the tissues of the nose. Further, the gas inside the mask provides cooling to and via softer tissues, such as those of the eye. As with the soft tissues within the nasal airway, cooling of the soft eye tissues can be passed to the brain and its vascular system, as no hard bone tissue or similar insulator interferes. Blood in the eye tissue drains by way of the ophthalmic veins through the sinuses, and thus cooled venous blood from the eye tissue drains adjacent the sinuses and brain tissue.

In a particular embodiment, a system 20 can be set up to provide a positive pressure of breathable gas for the patient. For example, regulator 32 may be set to outlet gas at a pressure sufficiently above atmospheric pressure so as to create a positive pressure, so that gas is always available when the patient inhales, and so that exhalation is generally or entirely channeled through the patient's mouth. Pressures above atmospheric pressure, such as 1.1 atmospheres (atm), 1.5 atm, 2.0 atm, or other pressures between 1.1 atm and 2.0 atm are believed to be advantageous in administering therapy as disclosed herein. As a particular example using mask 40', system 20 is set up to provide a positive pressure of about 1.5 atm within mask 40'. The positive pressure is accessible to the nose of the patient, while his or her mouth is adjacent or within atmospheric pressure (e.g. 1.0 atm). When the patient inhales, the positive pressure at his or her nose ensures that a substantial proportion (if not substantially all) of the inhaled gas comes through the nose and nasopharynx, because of the force of the positive pressure, and is thus the cooling breathable gas from system 20 rather than room temperature air. Further, if pressure is maintained, there is gas available for inhalation every time the patient breathes in. Every inhalation thus provides additional cooling gas to the nasopharynx and on to the patient's lungs. When the patient exhales, the path of least resistance to the exhalation is the mouth, where the pressure is significantly less than the positive pressure in mask 40' and/or in the patient's nasal airway. Consequently, gas that has been warmed in traveling to and from the patient's lungs is at least largely or completely kept from the nasopharynx and associated soft tissues. Such positive pressure can thus create a flow or circulation, from the space inside mask 40' through the nose and nasopharynx to the lungs, and from the lungs out through the mouth, with little or no exhalation into mask 40'. A consistent supply of cooling gas is provided to appropriate soft tissues at every inhalation, and the approach of warmer gases to those soft tissues is reduced or eliminated.

Mask 40, 40' may be of a plastic, substantially gas-impermeable material, and may be such as is used to provide oxygen to comatose or less-responsive patients, or the like. In other embodiments, mask 40, 40' may be of a more gas-permeable material or provided with vents or other openings so as to limit or prevent damage to the patient's facial skin during use over long periods. In embodiments in which mask 40 is not present, delivery tube 24 and/or nasal tubes 26, 28 may be held to the patient by a surgical or adhesive tape, clamp or other structure to minimize or prevent movement of tubes 24, 26, 28 with respect to the patient as the patient is moved or treated.

Insertion tubes 26, 28 are nasal tubes in the illustrated embodiment, each of a diameter adapted for insertion into a respective nostril (nare), and each of a length so that when properly inserted they extend beyond the anterior turbinate area (conchae) of the nose, bypassing the area in the nose that transfers the greatest amount of heat to inhaled air. Tubes 26 and 28 have their respective ends and outlets 54, 56 beyond the conchae, and in a particular embodiment between the conchae and the front of the sinus area (i.e. the rear portion of the nasal cavity), with the sphenoidal bone and associated cartilage and other tissue in that area. Tubes 26, 28 may (but need not) reach the back of the sinus region, as may be required or important for tubes that spray volatile coolants into or around the sinus cavities or that use balloons to hold coolant or block the airway.

Insertion tubes 26, 28 each have a single distal opening 54, 56 in the illustrated embodiment, in order to focus gas on a particular area proximate to the brain as indicated above. The single distal opening allows a consistent flow of gas to the desired area so as to continuously replace gas that has received heat (or transferred cooling) with new cooling gas. In other embodiments, additional openings may be provided, such as additional opening(s) at the distal end of tubes 26 and/or 28, or one or more openings in the side(s) of tubes 26 and/or 28. Additional or numerous openings in tubes 26 and/or 28, e.g. in the sides, can be provided. However, a single or fewer openings are effective in directing gas where it is needed, e.g. against the sphenoidal bone to focus cooling on the brain and vascular structures behind it, and further openings can spread gas toward tissues for which cooling is not desired or in directions that are less effective. Directed flow further obviates a need to artificially maintain the gas in a particular location, and assists the patient to inhale the provided gas naturally.

It should be noted that in therapy situations in which gas is administered, for example in which oxygen is provided to patients to increase oxygen richness or for other breathing assistance, gas is delivered either at a relatively high temperature (e.g. room temperature) as it enters tube(s) to the user, or are delivered through several feet or longer lengths of non-insulated tubing to allow ambient temperature to warm the gas to approximately room temperature before it gets to the patient. Further, tubes or masks providing the gas are designed to terminate at or just inside the nostrils' openings for user comfort and so that heat and moisture can be transferred to the incoming gas via the mucosa. Having the gas at approximately room temperature is important for the patient's comfort and for limiting effects of cold gas on tracheal, bronchial or lung tissue. In contrast, system 20 is designed to make sure the gas provided to the patient remains as cold as possible consistent with non-injurious cooling of tissue. Delivery tube 24 is accordingly maintained as short as possible, in some embodiments about one foot or less, and having insulating characteristics.

System 20 in a particular embodiment is a portable or ambulatory system, such as a kit (or part of a kit) that can be carried and used by an emergency medical technician, physician or other first-responder to an apparent health emergency. Such a kit may be kept on site at schools, businesses, public buildings, and the like in the same way as automated external defibrillators (AEDs) have been placed, e.g. mounted to a wall or positioned in a security or first aid area. In that configuration, system 20 may be used to treat a patient (e.g. victim of stroke or cardiac arrest) prior to the arrival of emergency help, and/or during transport to a hospital for additional treatment measures. For temporary help situations, canister 22 may be sized to provide a relatively short-term supply of gas, such as a size C or D gas cylinder or a cylinder of the size generally carried by firefighters or scuba divers. A somewhat larger canister 22 (e.g. a tank) or other source of compressed gas, with a longer-lasting supply, can be available in an ambulance or hospital. In either case, new gas canisters 22 can be provided to exchange with spent canisters 22 as treatment continues. It will be understood that the size and configuration of system 20 discussed above, in particular the short length of delivery tube 24 and portability of the small gas canisters, will be particularly useful for an ambulatory emergency system 20.

For ease in exchanging one canister 22 (e.g. an empty or smaller capacity canister) for another canister 22 (e.g. a full or larger capacity canister or tank), particular types of connections can be placed at a proximal end of delivery tube 24. As one example, a connection 60 on delivery tube 24 may be a standard connection for canisters holding a particular type of gas, e.g. a CGA connection for oxygen tanks. Such a connection reduces or eliminates the chance of connecting delivery tube 24 to an incorrect gas source, to an IV tube, or other potential hazard.

Alternatively or additionally, a Y-connection 64 or a stopcock 66 may be provided in delivery tube 24. If Y-connection 64 is used, separate canisters 22 (or their respective regulators or valves) can be connected to respective branches of connection 64. One canister can be opened for gas flow while the other remains closed. When that canister approaches or becomes empty, the second can be opened to continue the flow, while the empty canister is removed and replaced with a full canister. In such embodiments, a one-way valve (not shown) may be placed in each branch of Y-connection 64 so that gas does not escape through a branch disengaged from an empty canister.

Stopcock 66 is a two-way stopcock with two separate inlets connected to respective canisters 22, and an outlet connected to delivery tube 24. In such embodiments, both canisters 22 can be open. When stopcock 66 is in a position allowing flow from one of the canisters, flow from the other is blocked. As the canister approaches or reaches empty, stopcock can be turned to allow flow from the other canister, while the empty canister is removed and replaced. Y-connection 64 and/or stopcock 66 permit flow to continue through delivery tube 24 to the patient without significant interruption while empty canisters are replaced.

As noted above, delivery tube 24 can be constructed to be assembled to canister 22 prior to use of system 20, and that a connection on delivery tube 24 that allows easy attachment and detachment with canister 22 can be provided. In such embodiments, as a canister 22 approaches empty or otherwise cannot provide further gas cooled by a pressure drop, delivery tube 24 can be quickly and easily disconnected from that canister 22 and reattached to another canister 22, or flow can be obtained from a second canister via Y-connection 64 or stopcock 66. Thus, in an example in which a patient is being treated on-site, when cooling from a first canister 22 is exhausted, a second canister 22 may be attached. When an ambulance arrives, the delivery tube 24 may be disconnected from the on-site system 20 and connected to a system 20 on board the ambulance. Likewise, when the ambulance arrives at a hospital, if cooling is to be continued at the hospital delivery tube 24 may be disconnected from the ambulance's system 20 and connected to a system 20 in an operating room or other treatment area. It will be seen that such connectivity of delivery tube 24 may be provided at the end where delivery tube connects to canister 22 and/or valve of regulator 32, at a connection in the middle of delivery tube 24, or at the end of delivery tube that connects with mask 40 and/or insertion tubes 26, 28.

Figure 9:
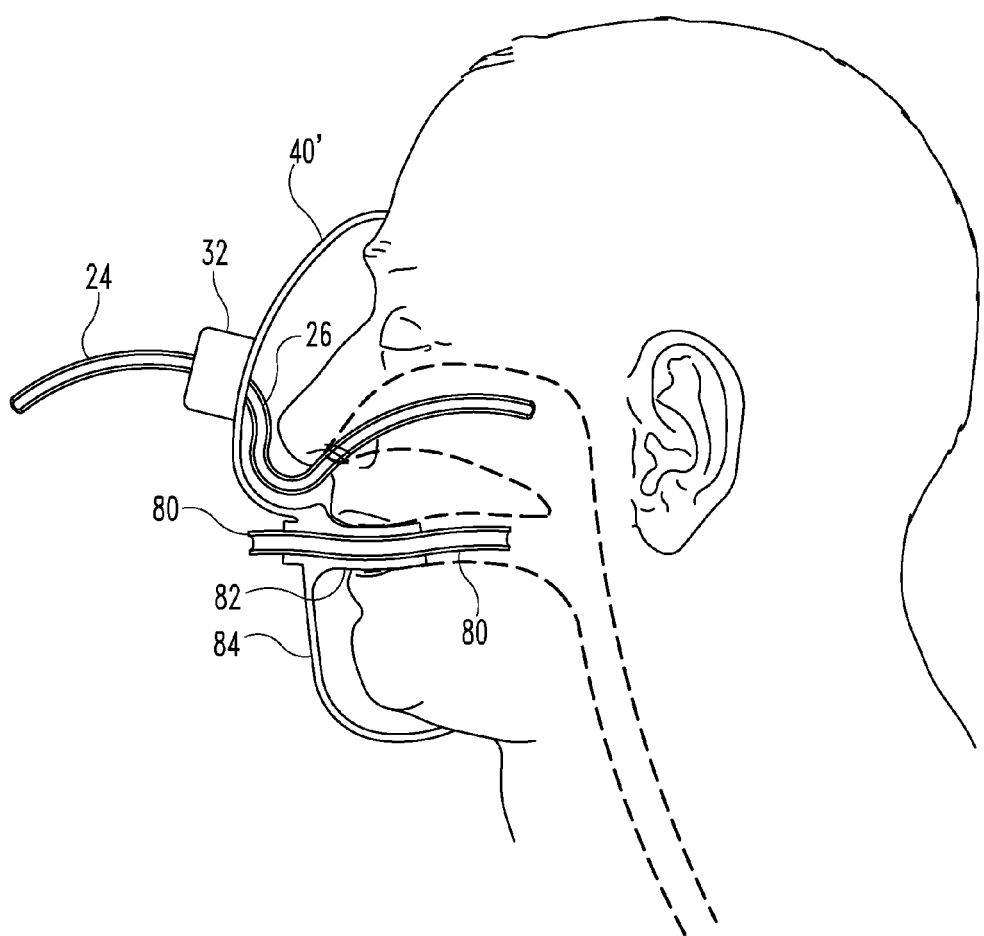
FIG. 9 is a schematic representation of a portion of the embodiment shown in FIG. 3B in cross section and applied to a patient.

It is also contemplated to include attachments to mask 40, 40' that may be useful in treating all patients, or those who are comatose, non-responsive (e.g. in cardiac and/or respiratory arrest) or have other difficulties. For example, FIG. 9 includes a representation of an embodiment of mask 40' that includes structure for maintaining an open mouth, including a tube 80 for insertion in to the mouth and along the tongue, a bite block 82 (which may be a part of or attached to tube 80), and lip or mouth coverings 84 (which also may be a part of or attached to bite block 82 and/or tube 80). Tube 80 generally maintains the oral cavity open for exhalation, and may also be used for insertion or attachment of equipment or instruments, and/or to facilitate artificial breathing during application of CPR, as the medical professional may desire. Bite block 82 maintains a spacing of the patient's teeth, both to keep the mouth open and to protect patient and medical professional from bite injuries. Coverings 84 generally cover the lips and nearby tissues, so as to shield the medical professional from bodily fluids from the patient. In addition to providing cooling gas via mask 40, 40', such structures provided as a part of or attached to mask 40, 40' can be fitted to the patient for safety and to maintain an open passage through the mouth. As noted above, maintaining that passage can provide for exhalation through the mouth via tube 80, and can thus provide a more efficient cooling for the patient. The embodiment of mask 40' includes an insertion tube 26 as described above, so that it will be seen that embodiments of mask 40' may include tubes 26 and/or 28, and embodiments of mask 40 may be provided without them.

In use, system 20 is applied to a patient, e.g. one diagnosed as having a traumatic head or brain injury, stroke, cardiac arrest, shock or other condition causing or leading to swelling or ischemia in the brain. In the illustrated embodiment, system 20 is provided with canister 22 already connected to or integral with delivery tube 24, and nasal tubes 26, 28 and mask 40 connected to delivery tube 24 as discussed above, prior to use. That is, system 20 is provided in a ready-to-use state. It will be understood that system 20 could also be provided with some assembly needed, such as assembly of delivery tube 24 to canister 22, or of mask 40 and/or nasal tubes to delivery tube 24. If assembly is needed, quick and secure connections as indicated above are preferred. Assembly (particularly of delivery tube 24 to canister 22) may be needed if gas canister 22 should be stored separately or remain unconnected to a conduit for safety reasons. Additionally, as noted above quick-connect or other easy connection(s) may be provided in one or both ends and/or the middle of delivery tube 24 so as to permit disconnection and reconnection of delivery tube 24 in connecting new gas sources to system 20.

Insertion tubes 26, 28 are placed through the respective nostrils of the patient as mask 40 is moved toward the patient's nose and mouth. Tubes 26, 28 are inserted further into the nasal cavity as mask 40 approaches the nose and mouth, so that the ends of tubes 26, 28 extend beyond the air-warming anterior turbinate area of the nose, e.g. to the front of the patient's choanae or sinus area, when mask 40 is positioned over the patient's nose and mouth. Although insertion tubes 26, 28 are intended to move through the nasal passage with little discomfort or resistance, one placing mask 40 and insertion tubes 26, 28 may apply a medical lubricant to the nostrils and adjacent tissues and/or nasal tubes 26, 28 if necessary. If lubricant is used, it should be assured that openings 54, 56 in nasal tubes 26, 28 are not obstructed. Strap 46 is placed around the patient's head to hold mask 40 against the patient's face and nasal tubes 26, 28 in static position within the nose and their ends adjacent the sinuses.

Gas flow from canister 22 may be started prior to or after placement of tubes 26, 28 within the patient, but starting flow after placement may make placement easier through having no resistance or force from the gas flow to contend with. When canister 22 is opened, e.g. by opening valve or regulator 32, gas moves from canister 22 into delivery tube 24. As the pressurized gas leaves canister 22 and enters delivery tube 24, the drop in pressure provides a concomitant drop in temperature of the gas. The gas in delivery tube 24 is thus at a temperature substantially below room or ambient temperature and body temperature, and in particular embodiments is between 0° Celsius and 20° Celsius, such as around 0° Celsius. As discussed above, delivery tube 24 is configured to reduce or prevent substantial heat gain and preserve the negative thermal energy of the gas as it passes along tube 24, by limiting the length of tube 24 to a minimum, for example one foot, and/or by insulating tube 24. With the length of insertion tubes 26, 28 lengthened as compared to oxygen therapy systems to limit warming of the gas by the nasal cavity, the gas is moved through delivery tube 24 and into and through insertion tubes 26, 28 so that it remains cool. For example, the gas has a temperature not less than its temperature at the proximal end of delivery tube 24 (assuming no refrigeration along delivery tube 24) as it exits tubes 26, 28, and is desirably at approximately the same temperature it had at the proximal end of delivery tube 24. The exit temperature of the gas should be within 20 Celsius degrees of its temperature in the proximal end of delivery tube 24, more desirably within 0 to 5 degrees of that initial temperature, so as to provide a low enough exit temperature to provide sufficient cooling to tissue. No external refrigeration, pumps or other equipment are needed in this embodiment to cool or maintain the low temperature of the gas or to propel it or ensure its composition, making this embodiment of system 20 non-electrical, although such additional equipment could be used in other embodiments. In the illustrated embodiment, the pressure drop from canister 22 to tube 24 provides a cooled gas, tubes 24, 26 and 28 maintain the coolness or negative thermal energy level of the gas, and pressure from canister 22 moves the gas to the therapy site.

The low temperature gas is released through openings 54, 56 in nasal tubes 26, 28 into an area adjacent the brain, such as the choanae and/or nasopharynx, adjacent the sphenoid bone and sinus. The gas transfers its negative thermal energy to, or receives heat from, tissues proximate to the brain such as the sphenoid bone and sinus and adjacent tissues. A temperature gradient, between the gas and the tissues it contacts on one hand and brain tissue and blood vessels leading to the brain on the other, is created which reduces the temperature of blood flowing to and within the brain and brain tissue. Gas from canister 22 continues flowing as long as the administrator of treatment desires, funneling a continuing supply of cold gas to the base of the brain. The supply can be reduced when a desired brain temperature or a desired temperature reduction has been reached, so that the gas delivered to the choanae does not further reduce but merely maintains the temperature at the desired level. For example, a lowering of brain temperature of as much as 5 Celsius degrees, in particular embodiments of at least 3 to 4 Celsius degrees, may be sought to decrease or inhibit swelling of the brain tissue or reduce the onset or effects of ischemia. It has been found clinically that an improved outcome will be achieved if the temperature is lowered by at least 3 to 4 Celsius degrees. In other embodiments, a change of at least 1 to 2 Celsius degrees can provide benefit. Treatment with system 20 can cease when the treatment is no longer effective or necessary, as when it would interfere with surgery or other treatment, or when other treatments have concluded and a return to normal temperature and brain function is desired.

The above discussion identified particularly mask 40 in describing the use of system 20. It will be understood that the use of embodiments such as mask 40' will be quite similar. To summarize, mask 40' may be provided pre-connected to delivery tube 24 and canister 22, or may be connected at the time of use. Mask 40' is fitted on the patient's head with strap 46' as indicated above, without insertion of tube(s) into the patient's nose in embodiments of mask 40' that do not include such tubes. Flow of gas is begun, with the cooling gas at the desired temperature (and perhaps at a pressure above atmospheric pressure, as described herein) entering mask 40'. Treatment occurs largely as noted previously, with gas cooling soft tissues (e.g. tissues within the nasal airway or eye tissue) adjacent the brain. When the desired cooling effect has been achieved, flow can be reduced to maintain the level of cooling, or stopped when cooling is no longer needed.

Although molecular oxygen and nitrogen have been suggested above as gases for use in system 20, other gases palatable to humans may be used, such as a nitrogen/oxygen mix, heliox, or air. With such palatable gases and the arrangement of structures as noted above, the tissues and/or natural breathing processes of the patient will absorb or take in some or all of the gas for use in the body. Use of such gases obviates the need for system 20 to include an exhaust line or other structure for removing gas or other substances from the patient. Possibilities of hypoxia, toxic effect from liquids or other chemicals, and other negative effects are reduced or substantially eliminated, although good medical practice may dictate that the user of system 20 monitor the patient for abnormalities in body gases or chemistry.

For monitoring the patient, system 20 may include one or more monitors or sensors 70. In the illustrated embodiment, sensor 70 is connected to the end of one of insertion tubes 26, 28, and in other embodiments it will be understood that sensor 70 may be placed in other appropriate locations, e.g. on or in tube 24 or a mask. Likewise, if more than one sensor 70 is provided, they may all be on one tube 26, 28, split between them, or otherwise positioned or attached with respect to the patient or system 20. Sensor 70 may be directed to any of a number of factors or conditions associated with the use of system 20. For example, sensor 70 may be a flow rate monitor or sensor in the flow of gas in tube 26 and/or 28. As another example, sensor 70 may be a temperature sensor (such as an infrared sensor) along the outside of tube 26 and/or 28 and positioned against or within a mask, tissue or cavities (e.g. a sinus) to monitor temperature of the gas or tissues (e.g. those next to the brain or the brain cavity). Such a temperature sensor is along the outside of tube 26 and/or 28 (or through a second lumen if tube 26 and/or 28 is a dual-lumen tube), or within the space between a mask and the patient's face to obtain readings representative of gas or tissue temperature and to keep the temperature sensor out of gas flow if desired.

Sensor(s) 70 are connected via hard-wire, wireless or other connection (indicated by dashed lines in FIG. 5) to read-out(s) 72 accessible to the user. As the user or observer (e.g. physician or emergency technician) monitors such read-out(s) 72, he or she can adjust system 20 as desired or necessary. For example, if sensor 70 is a flow rate sensor, it will give the user notification of decreasing flow indicative of a low gas supply in canister 22 or other flow-inhibiting or -reducing problem. If sensor 70 is a tissue-temperature sensor, it will give the user notification of temperature decreases or increases, and the user can adjust flow to maintain a desired cooled temperature or to change the temperature to a desired level. Based on flow and gas temperature, a target amount or duration of gas flow can be calculated so that at least an approximate period of use of system 20 to achieve a desired cooling effect is derived. The use of system 20 over that period should have the desired effect, and further monitoring of sensor(s) 70 can help the user maintain the effect.

One or more such readouts 72 may be provided to the user on a monitor screen, a hand-held screen, or other types of read-out display. A particular example is a display (e.g. screen, LCD, etc.) mounted on or fixed to mask 40'. Such a display is fixed to a side surface or top surface of mask 40' in a location and position that does not impair the observation of the patient's eyes. That is, when the observer or user is focused on the patient's face, both the patient's eyes and readout(s) 72 are within the field of vision of the observer. Such placement is advantageous at least because it permits easy observation of both the patient's eyes and the display at the same time.

The description above described placement of insertion tubes 26, 28 through the nostrils to a position at which the gas transferred through tubes 26, 28 is at or about the temperature it has in delivery tube 24. It will be understood that in other embodiments of system 20, tube 26 and/or 28 can be inserted through the mouth, a tracheotomy or other opening and curved upward into or through the nasopharynx to deliver cool gas. In such embodiments, a single tube 26 might be provided, since only one body opening (rather than two nostrils) are available for placement. Further, the tube(s) 26 and/or 28 may be somewhat longer for placement through the mouth or other opening, and placement should be carefully made in light of the potential for activating the gag reflex.

Applying gas to the inside space of a mask, i.e. the airtight space between a mask and the patient's face provides cooling as well. The eyes and other external soft tissue of the head, just as with internal soft tissue, can be cooled in this way to reduce the temperature of adjacent brain tissue. Such a method can provide both internal cooling, via inhalation of cooling gas, and external cooling focused on the head's external soft tissues.

In such embodiments, the use of breathable gases provides both cooling and support for the patient's respiration. As already noted, existing respiration support systems ensure that administered gases are comfortable to the patient, e.g. so that they do not experience the "brain freeze" phenomenon sometimes felt when frozen foods or cold drinks are held in the mouth adjacent the palate. Accordingly, such systems will commonly use long tubes and/or electric or other heating elements associated with the gas-delivery tube in order to raise the gas temperature to a comfortable level, e.g. above room temperature. The present disclosure is intended to provide the opposite result of cooling to a degree that may cause discomfort to a patient, if the patient is conscious, so as to cool the brain tissue. Use of breathable gas is also beneficial in terms of supplying enrichment to the body during a cardiovascular event. During such events, blood flow is reduced, which consequently reduces the amount of oxygen reaching the cells. Providing a steady flow of breathable gas as in the present disclosure can increase the oxygen concentration in the blood. At least part of the negative effect of blood flow reduction can be compensated for by a higher oxygen concentration. The embodiment noted above that provides a positive pressure in a mask (e.g. mask 40') may be particularly useful in increasing oxygen concentration in the blood.

The above description also focused principally on the use of system 20 to cool the brain so as to minimize damage to the brain. It will be understood that system 20 can be applied to a patient in order to cool the brain and reduce its function in appropriate therapeutic situations other than minimizing damage from ischemia or swelling. Further, in situations in which another organ or body tissue or part should be cooled to minimize damage from ischemia or for other therapeutic reasons, system 20 can be used to provide direct cooling. In such a case, insertion tubes 26, 28 and/or mask 40 may not be necessary, and may be discarded if provided. Delivery tube 24, insertion tube(s) 26 and/or 28, or other conduit connected to delivery tube 24 may be inserted into the patient via a natural orifice, wound, incision or other opening to the site where cooling is desired. Application of gas through delivery tube 24 provides cooling, as discussed above.

While the disclosure has been illustrated and described in detail in the drawings and foregoing description, the same is to be considered as illustrative and not restrictive in character, it being understood that only the preferred embodiment has been shown and described and that all changes and modifications that come within the spirit of the disclosure are desired to be protected. It will be evident from the specification that aspects or features discussed in one context or embodiment will be applicable in other contexts or embodiments.

What is claimed is:

1. A system for therapeutic cooling of a patient, comprising:
   a mask having a strap and a hole, said mask being adapted to cover at least the patient's nose and to be held to the patient's head by said strap, so that when said mask rests against the patient's face a space between at least a portion of the patient's face and said mask exists;
   a source of coolant, said coolant consisting essentially of compressed breathable gas, wherein a flow path extends from said source through said hole of said mask;
   a regulator in said flow path between said coolant source and said hole of said mask; and
   a delivery tube having a lumen defining at least part of said flow path for said coolant, for conducting said coolant toward said mask;
   wherein said coolant is cooled adiabatically on or after release from said source, and wherein first and second insertion tubes are connected to said delivery tube, each extending to a respective free end having an opening, said insertion tubes sized and configured to be inserted into respective nares of a patient's nose so that said free ends are positioned in the airway beyond the anterior turbinate area of the patient's nose, so that the gas passes the mucosa and conchae of the nose before exiting said insertion tubes, wherein at least one of said delivery tube and at least one insertion tube extend through said hole of said mask so that said mask rests against the patient's face when said at least one insertion tube is inserted into the patient's nose.

2. The system of claim 1, wherein said source is a canister of compressed breathable gas.

3. The system of claim 1, wherein a configuration of said delivery tube includes forming said delivery tube of foam insulation.

4. The system of claim 1, wherein a configuration of said delivery tube includes forming said delivery tube of an internal plastic lumen with an outer layer of foam insulation.

5. The system of claim 1, wherein said source includes two compressed gas canisters, and further comprising a Y-shaped connector connected to said delivery tube and to each of said canisters.

6. The system of claim 1, wherein said source includes two compressed gas canisters, and further comprising a two-way stopcock connected to each of said canisters and to said delivery tube.

7. The system of claim 1, wherein said regulator is fixed to said mask so that an output of said regulator communicates with said hole of said mask, so that adiabatically-cooled gas from said regulator enters said mask.

8. The system of claim 1, wherein said delivery tube is a high-pressure tube from said source to said regulator.

9. The system of claim 1, wherein said mask is adapted to cover the eyes of a patient.

10. The system of claim 1, wherein said mask is a full-face mask.

11. The system of claim 1, wherein said mask is adapted to cover the mouth of the patient.

12. The system of claim 1, further comprising a sensor connected to one or more of said delivery tube, regulator and mask, and a readout communicatively connected to said sensor, said readout providing an indication of at least one of temperature and pressure of said coolant.

13. The system of claim 12, wherein said readout is fixed to said mask and said mask permits observation of the patient's eyes when fitted to the patient, and wherein the patient's eyes and said readout are both within an observer's field of vision when said mask is fitted to the patient.

14. A system for cooling the brain with compressed gas, comprising:
a supply of a compressed breathable gas for thermal transfer with tissues in a patient's head, said gas provided in at least one canister initially at a first pressure greater than atmospheric pressure;
a mask for fitting over a patient's face to cover at least the patient's nose and eyes, said mask having a regulator fitted thereto;
a high-pressure delivery tube connecting said at least one canister with said regulator, said delivery tube configured such that gas traveling along said delivery tube remains at approximately the same temperature along said tube,
wherein said gas is cooled adiabatically to a first temperature below room temperature, and said gas flows into said mask at approximately the first temperature to cool tissues adjacent the brain cavity, and wherein a set of first and second nasal tubes is at least partially within said mask, each said nasal tube for insertion into a respective nostril of a patient, said first and second nasal tubes each having a respective distal end with a respective hole, and each being sized and configured so that when said first and second nasal tubes are fully inserted into the patient, said respective distal ends are positioned in one or more of the choanae of the patient, without closing an airway through either nostril.

15. The system of claim 14, wherein said first temperature is between 0 and 20 degrees Celsius.

16. The system of claim 14, wherein said supply of breathable gas is sufficient in flow, temperature and duration to cool at least a portion of the brain by about 1 to 5 Celsius degrees.

17. The system of claim 14, wherein said supply is provided by multiple canisters of compressed gas, and wherein said delivery tube is adapted to easily accept flow from multiple canisters.

18. The system of claim 14, wherein said delivery tube is connected to a stopcock, and said stopcock is connected to said multiple canisters of compressed gas, wherein said stopcock is operable to switch flow into said delivery tube between or among said multiple canisters.

19. The system of claim 14, wherein a configuration of said delivery tube includes a layer of insulation incorporated in or on said delivery tube.

20. The system of claim 14, further comprising at least one sensor for detecting at least one of a flow rate in said delivery tube and a temperature of said gas, and at least one readout communicatively connected to said at least one sensor for displaying information derived from said sensor to an external observer, wherein said readout is fixed to said mask.

21. A cooling system for applying localized hypothermic treatment, comprising:
a heat-transfer medium consisting essentially of a breathable gas, said gas supplied in at least one canister at a pressure greater than atmospheric pressure;
a delivery tube connected to said canister, said delivery tube configured so that said gas can travel along said delivery tube without a significant change in temperature of said gas along said length;
a mask having a regulator connected to said delivery tube so that output of said regulator flows into said mask, said mask further having a readout display attached thereto, said readout display showing information related to the operation of the system;
a stopcock connected to said delivery tube, said stopcock being operable to change flow into said delivery tube from a first said canister to a second said canister; and
a pair of insertion tubes connected to said delivery tube and sized and configured so that respective distal ends of each of said insertion tubes are in the choanae of the patient when said insertion tubes are fully inserted into the patient, wherein said insertion tubes each have a single outlet at said respective distal ends of said insertion tubes, whereby said gas exits said tubes in one direction.

22. The system of claim 21, wherein said canister is of a hand-portable size and weight, so that said system is carryable to a patient by an emergency responder.

23. The system of claim 21, wherein a configuration of said delivery tube includes said delivery tube being formed entirely of a foam insulation.

* * * * *